(12) United States Patent
Nakajima et al.

(10) Patent No.: US 9,420,820 B2
(45) Date of Patent: Aug. 23, 2016

(54) METHOD FOR ISOLATING POLYPHENOLS FROM OLIVE MILL WATER

(71) Applicants: University of Tsukuba, Tsukuba-Shi (JP); Center of Biotechnology of Sfax, University of Sfax, MESRS, Sfax (TN)

(72) Inventors: Mitsutoshi Nakajima, Tsukuba (JP); Marcos Neves, Tsukuba (JP); Hiroko Isoda, Tsukuba (JP); Ilyes Dammak, Sfax (TN); Sami Sayadi, Sfax (TN)

(73) Assignees: University of Tsukuba, Tsukuba-shi (JP); Center of Biotechnology of Sfax, University of Sfax, MESRS, Sfax (TN)

( * ) Notice: Subject to any disclaimer, the term of this patent is extended or adjusted under 35 U.S.C. 154(b) by 321 days.

(21) Appl. No.: 13/963,120

(22) Filed: Aug. 9, 2013

(65) Prior Publication Data

US 2015/0045449 A1  Feb. 12, 2015

(51) Int. Cl.
*A61K 36/63* (2006.01)
*A23L 1/30* (2006.01)

(52) U.S. Cl.
CPC ............... *A23L 1/3002* (2013.01); *A61K 36/63* (2013.01); *A61K 2236/00* (2013.01)

(58) Field of Classification Search
CPC ........................................................ A61K 36/63
USPC ................................................. 424/769, 777
See application file for complete search history.

(56) References Cited

U.S. PATENT DOCUMENTS

| | | | |
|---|---|---|---|
| 4,879,042 A | 11/1989 | Hanson et al. | |
| 6,358,542 B2 | 3/2002 | Cuomo et al. | |
| 6,379,696 B1 | 4/2002 | Asmussen et al. | |
| 7,261,909 B2 | 8/2007 | Crea | |
| 2002/0004077 A1 | 1/2002 | Cuomo et al. | |
| 2002/0058078 A1 | 5/2002 | Crea | |
| 2002/0198415 A1 | 12/2002 | Crea | |
| 2007/0020350 A1* | 1/2007 | Numano | A61K 36/63 424/769 |
| 2008/0014322 A1* | 1/2008 | Ibarra | A23L 1/2126 426/330.6 |
| 2008/0146828 A1* | 6/2008 | Benavent | A23K 1/146 554/177 |
| 2008/0179246 A1* | 7/2008 | De Magalhaes Nunes Da Ponte | A23L 1/3002 210/637 |
| 2010/0047887 A1* | 2/2010 | Achkar | C12P 7/22 435/156 |
| 2010/0069313 A1* | 3/2010 | Ulm | A23L 1/0035 514/27 |
| 2010/0240769 A1* | 9/2010 | Tornberg | A23L 1/0524 514/735 |
| 2013/0108716 A1* | 5/2013 | Crea | A23L 1/2115 424/725 |

FOREIGN PATENT DOCUMENTS

| | | |
|---|---|---|
| CA | 2420893 A1 | 3/2002 |
| EP | 0811678 A1 | 12/1997 |
| EP | 1310175 A2 | 5/2003 |
| EP | 1369407 A1 | 12/2003 |
| EP | 1773721 A1 | 4/2007 |
| ES | 2051238 A1 | 6/1994 |
| FR | 2825022 A1 | 11/2002 |
| JP | 2000319161 A | 11/2000 |
| WO | WO-9747711 A1 | 12/1997 |
| WO | WO-0145514 A1 | 6/2001 |
| WO | WO-0212159 A1 | 2/2002 |
| WO | WO-0218310 A1 | 3/2002 |
| WO | WO-02064537 A1 | 8/2002 |
| WO | WO-2005003037 A1 | 1/2005 |

OTHER PUBLICATIONS

Beckmann (1999) Nucleation phenomena during the crystallisation and precipitation of Abecarnil. Journal of crystal growth 198, 1307-1314.

Berry, et al. (1997) Synthesis of drowning-out crystallization-based separations. AIChE Journal 43(1), 91-103.

Bertin et al. (2011) Recovery of high added value natural polyphenols from actual olive mill wastewater through solid phase extraction. Chemical Engineering Journal.

Brittain (1999) Polymorphism in pharmaceutical solids, M. Dekker New York.

Charmolue et al. (1991) L-serine obtained by methanol addition in batch crystallization. AIChE Journal 37(8), 1121-1128.

Ferri et al. (2011) Recovery of low molecular weight phenols through solid-phase extraction. Chemical Engineering Journal 166(3), 994-1001.

Henley et al. (1981) Equilibrium-stage separation operations in chemical engineering, Wiley New York.

Hyung et al. (2008) Drowning-out crystallization of l-proline: Effect of anti-solvent composition and processing parameters on crystal size and shape. Powder technology 186(2), 137-144.

(Continued)

*Primary Examiner* — Chris R Tate
(74) *Attorney, Agent, or Firm* — Locke Lord LLP (57) ABSTRACT

The present invention relate to a highly efficient and novel method, using clean technologies, for obtaining a natural bioactive concentrate that is rich on polyphenols from olive mill water (OMW). The clean technologies integrate centrifugation, a drowning-out crystallization-based separation process, and vacuum evaporation. The method provides a highly-concentrated polyphenol isolate (up to 99% (mass fraction)) from other components presents in OMW, with up to half of the polyphenol content being hydroxytyrosol. The isolated polyphenols exhibit anti-oxidant, anti-microbial, anti-inflammatory, and anti-carcinogenic activities; they can be prepared as solid particles, as an aqueous solution, in an emulsion, or as lipidic-based nanoparticles. The isolated polyphenols can be used in the food industry, cosmetic industry, or pharmaceutical industry.

7 Claims, 11 Drawing Sheets

(56) References Cited

OTHER PUBLICATIONS

Mantzavinos et al. (2005) Treatment of olive mill effluents:: Part I. Organic matter degradation by chemical and biological processes—an overview. Environment international 31(2), 289-295.

Moure et al. (2001) Natural antioxidants from residual sources. Food Chemistry 72(2), 145-171.

Myerson (2002) Handbook of industrial crystallization, Butterworth-Heinemann.

Ntaikou et al. (2009) Exploitation of olive oil mill wastewater for combined biohydrogen and biopolymers production. Bioresource Technology 100(15), 3724-3730.

Obied et al. (2005) Bioactivity and analysis of biophenols recovered from olive mill waste. J. Agric. Food Chem., 53: 823-837.

Pennington (2002) Food composition databases for bioactive food components. Journal of food composition and analysis 15(4), 419-434.

Randhir et al. (2007) Mung beans processed by solid-state bioconversion improves phenolic content and functionality relevant for diabetes and ulcer management. Innovative Food Science & Emerging Technologies 8(2), 197-204.

Rodis et al. (2002) Partitioning of olive oil antioxidants between oil and water phases. Journal of Agricultural and Food Chemistry 50(3), 596-601.

Schieber et al. (2001) By-products of plant food processing as a source of functional compounds—recent developments. Trends in Food Science & Technology 12(11), 401-413.

Schmitt et al. (1999) Nucleation and crystallization kinetics of hydrated amorphous lactose above the glass transition temperature. Journal of pharmaceutical sciences 88(3), 291-296.

Szabó-Révész et al. (2001) Development of spherical crystal agglomerates of an aspartic acid salt for direct tablet making. Powder technology 114(1), 118-124.

Takaç et al. (2009) Recovery of phenolic antioxidants from olive mill wastewater. Recent Pat. Chem. Eng. 2, 230-237.

Visioli et al. (2002) Biological properties of olive oil phytochemicals. Critical reviews in food science and nutrition 42(3), 209-221.

Visiol et al. (2002) Antioxidant and other biological activities of phenols from olives and olive oil. Medicinal Research Reviews 22, 65-75.

\* cited by examiner

METHOD FOR ISOLATING POLYPHENOLS FROM OLIVE MILL WATER

BACKGROUND OF THE INVENTION

Olive mill water (OMW) is a liquid waste produced during olive oil extraction from olive fruits. Annual OMW production is estimated to be over 20 million m$^3$; this represents a huge environmental problem, not only due to the large amounts produced, but also because OMW contains phytotoxic compounds. However, OMW is a rich source of a diverse range of polyphenols having a wide array of biological activities with recognized uses in the food and pharmaceutical industries. Indeed, OMW has 300 to 500 times higher levels of polyphenols than in extracted oil. Accordingly, recovery of polyphenols from OMW has economic value provided that they can be efficiently obtained.

Experimental data disclosed herein demonstrate evidence of successful application of a novel and efficient method for isolating polyphenols from OMW to obtain biomolecules of interest for the food industry, cosmetic industry, or pharmaceutical industry.

SUMMARY OF THE INVENTION

As described below, the present invention features efficient and novel methods for isolating polyphenols from olive mill water (OMW).

In one aspect, the invention provides a method for isolating polyphenols from olive mill water (OMW). The method includes steps of obtaining an OMW after olive oil extraction from olive fruits; pretreating the OMW by removing residual oil, large-sized organic compounds, particles, or soluble molecules from OMW thereby forming a more clear aqueous phase; concentrating the aqueous phase thereby preparing a concentrate; mixing the concentrate with solvent thereby producing a mixture; transferring the mixture to a crystallization unit for isolating a liquid phase; and transferring the liquid phase to a distillation unit for evaporating the solvent and for retaining a polyphenol-enriched aqueous solution.

The solvent can be ethanol (EtOH), e.g., 95% (v/v) EtOH.

In certain embodiments, pretreating means centrifuging or filtering. Centrifuging can occur at 3000 to 6000×g, e.g., 5380×g, for 30 to 60 minutes. OMW can be fed into a centrifuge in a continuous, semi-continuous, or batch mode.

In particular embodiments, the pH of an aqueous phase is adjusted to between 3.9 and 4.1, e.g., a pH of 4.0.

In some embodiments, the aqueous phase is concentrated by flash evaporation. Flash evaporation can occur at 0.15 bar and 42° C. The concentrate can comprise hydroxytyrosol, oleuropein, caffeic acid, and other minor polyphenols. The final concentration of dissolved solids in the concentrate can be 40 to 70% (w/w) and contain 60 to 90% organic matter fraction, e.g., 60%.

In certain embodiments, the mixing step occurs in one or more mixing modules; the one or more mixing modules can be arranged in parallel. The mixture can have a final solvent mass fraction that is specified by an operator. The concentrate can be mixed with 50 to 99% EtOH (v/v), e.g., 95% EtOH. Dissolved carbohydrates and dissolved salts can be precipitated out in the crystallization unit, as a solid phase. The solid phase comprising a high content of salts and saccharides can be used in a food, cosmetic, or pharmaceutical composition. The one or more mixing modules and the crystallization unit can have independently controllable environments including temperature, solvent mass fraction, and numbers of stages.

In some embodiments, evaporating a solvent occurs at an absolute pressure of 0.15 to 0.55 bar, e.g., 0.15 bar, and a temperature of 30 to 50° C., e.g., 45° C. The vapor rate can be about 1310 kmol/h, molar fraction distilled 85% and reflux ratio of 10. The evaporated solvent can be distilled and recycled for later use.

In any of the above embodiments, a polyphenol-enriched aqueous solution is prepared. The polyphenol-enriched aqueous solution can be used in a food, cosmetic, or pharmaceutical composition. One or more polyphenols can be isolated from the polyphenol-enriched aqueous solution. The one or more isolated polyphenols can be used in a food, cosmetic, or pharmaceutical composition. The one or more isolated polyphenols can be substantially water free.

The above embodiments can be combined in any possible manner.

The present invention, at least, produces a concentrated aqueous solution enriched of polyphenols. The novel method disclosed herein provides the isolation, in a final product, of most polyphenols present in OMW and with high purity; in particular, hydroxytyrosol, the most powerful antioxidant, represents about 25% wt. of the total polyphenols present in the final product.

The isolated polyphenols exhibit many biological activities, in particular: anti-oxidant, anti-microbial, anti-inflammatory, and anti-carcinogenic activities; they can be prepared as solid particles, as an aqueous solution, in an emulsion, and as lipidic-based nanoparticles. They can be used in compositions for the food industry, cosmetic industry, or pharmaceutical industry.

Other features and advantages of the invention will be apparent from the Detailed Description and from the claims.

DEFINITIONS

Unless defined otherwise, all technical and scientific terms used herein have the meaning commonly understood by a person skilled in the art to which this invention belongs. As used herein, the following terms have the meanings ascribed to them below, unless specified otherwise.

Drowning-out or salting-out crystallization is a method for crystallizing a solute from a super saturated solution by adding an anti-solvent, which reduces the solubility of the solute. This method is used for highly soluble materials rather than evaporative or cooling crystallization, which have weak solubility temperature dependence (Berry et al. 1997). It is suitable for the separation of heat labile material because crystallization can occur at a lower temperature. The use of an anti-solvent to precipitate amino acids is quite common. Such crystallization methods are widely used for the separation of pharmaceutical products and biomaterials in industrial processes (Beckmann 1999; Myerson 2002).

Flash (or single-stage distillation) evaporation process is a single-stage distillation in which a feed is partially vaporized to give a vapor that is enriched for the more volatile components (Henley and Seader 1981).

Nucleation is the step where solutes dispersed in a solvent gather into clusters, on the nanometer scale (which elevates solute concentration in a small region) and become stable clusters. These stable clusters constitute the nuclei. However, when the clusters are not stable, they dissolve. Clusters need to reach a critical size to become stable nuclei. Such critical size is dictated by the operating conditions.

Olive mill water (OMW) is the mixture of water contained in an olive fruit (vegetation water) and water used during olive oil processing (e.g., washing and processing). OMW is also known as alpechin, margine, and jamila.

Polyphenols are a major group of natural products that occur in tissues of all higher plants. Polyphenols are characterized by the presence of large multiples of phenol structural units. The number and characteristics of these phenol structures underline the unique physical, chemical, and biological (e.g., metabolic, toxic, and therapeutic) properties of particular members of the class. They may be broadly classified as phenolic acids, flavonoids, stilbenes, and lignans. Of the various plants, the olive (*Olea europaea* L.) has been recognized as a good source of polyphenols (Pennington 2002; Visioli and Galli 2002) and most drug compendia (European, Japanese, British, and French pharmacopoeias and The United States National Formulary) contain olive oil monographs, whereas the French pharmacopoeia also includes an olive leaves monograph.

Unit procedure is defined as a sequence of actions (called operations) taking place within the same piece of equipment.

Three-phase continuous system is a method for increasing processing capacity, efficiency, and yield of an olive oil production facility. The three-phase continuous systems can process 30-32 tons per day with a fraction of the labor requirement. However, this technology also uses 50% more water than the simple pressing system (average 80-100 L of water per 100 kg of fruit processed) and generates twice as much OMW per unit mass of fruit processed (1.3-2 L/kg compared to 0.5-1 L/kg in the classical system).

Total Dissolved Solid (TDS) is a measure of the combined content of all inorganic and organic substances contained in a liquid in molecular, ionized, or micro granular (colloidal sol) suspended form. Generally the solids must be small enough to avoid being trapped in a two-micrometer (nominal size or smaller) pore size filter.

Water flow is the amount of water available in a water supply system.

As used herein, "obtaining" includes collecting, harvesting, purchasing, synthesizing, or otherwise acquiring matter.

Unless specifically stated or obvious from context, as used herein, the term "or" is understood to be inclusive. Unless specifically stated or obvious from context, as used herein, the terms "a", "an", and "the" are understood to be singular or plural.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. Ranges from 50 to 100 include similar steps. Ranges between 100 and 200, 200 and 300, 300 and 400, and so forth also include similar steps.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any method or composition provided herein can be combined with one or more of any of the other methods and compositions provided herein.

DETAILED DESCRIPTION OF THE INVENTION

The present invention features novel and efficient methods that are useful for isolating polyphenols from olive mill water (OMW) and for obtaining a concentrated aqueous solution enriched of polyphenols produced by the novel and efficient methods.

The invention is based, at least in part, on an increased understanding of the mechanisms of molecular aggregation, organization, and crystallization of solute from solution. By sophisticated control of such variables as temperature, agitation, pH, ionic strength, ion valency, and solvent/nonsolvent ratio and the dynamics of time-variation of these parameters, it is possible to selectively precipitate single solute species as small, dense, quasicrystalline particles virtually devoid of entrapped contaminants. Separation of these particles from the suspending medium by membrane filtration or centrifugation allows recovery of single species in extraordinarily high purity and concentration. Additionally, the invention produces a final product that is virtually free from harmful contaminants, such as organic solvent. Instead, the present invention uses ethanol (EtOH) as a solvent, which is food grade component in food production. Other solvents, such as methanol and isopropanol, can be used. The present invention overcomes many obstacles present in current separation technologies for producing a safe food product.

This present invention relates to a process for isolating polyphenols from OMW, combining different process units: centrifugation, flash evaporation, drowning-out crystallization-based separation process, and distillation, for the isolation of polyphenols from the TDS in OMW based on the solubility behavior changing after addition of EtOH as solvent chosen in the present invention. Further, distillation process unit is applied for the regeneration of EtOH which is used in a later process.

Here, is disclosed a new integrated process for the isolation of polyphenols from OMW.

The process flow pattern of the present invention is composed of preliminary centrifugation of OMW (G-force 5380× g) which allows the reduction of 45% wt. of total organic matter mostly composed of carbohydrates and oil. The aqueous supernatant phase is flash evaporated to increase the subsequent crystallization nucleation rate (Schmitt et al. 1999). This step allows achievement of 60% (mass fraction) of solid concentrate. Moreover, almost all polyphenols present in OMW are recovered in the produced concentrate. The method is conducted, in batch mode, to show the influence of EtOH mass fraction on the purity of polyphenols. Here, the concentration of polyphenols in the system is kept constant, while the EtOH mass fraction in the crystallizer is varied, at room temperature. Total polyphenols purity increases with increasing EtOH mass fraction in the system.

Maximum polyphenols purity is attained for 90% wt. EtOH mass fraction or greater. Thus, drowning-out of carbohydrates and most minerals, from water, using EtOH as antisolvent offers an opportunity to achieve high polyphenols purity.

A concentrated aqueous solution enriched of polyphenols is obtained as final product of the present invention. In particular, the novel method disclosed herein provides isolation, in a final product, of most polyphenols present in OMW, with high purity and reaching more than 95% wt; in particular, hydroxytyrosol, the most powerful antioxidant, represents about 25% wt. of the total polyphenols isolated.

The production of functional foods from the obtained final product constitutes a viable alternative for transforming this agro-industrial waste stream into a useful and relevant food ingredient. Also, the application of polyphenols in cosmetics has grown rapidly in recent years, many cosmetic products containing polyphenols are sold on the market. They are particularly useful in the context of skin anti-aging e.g. polyphenols from OMW is used to prepare a skin cosmetic causing no skin irritancy and having excellent rough skin preventive effect (JP2000319161, 2000). This skin cosmetic may be formulated, as necessary, with various ingredients generally used in cosmetic compositions, and can be prepared into any formulation such as ointment, lotion, milky lotion, pack, cataplasm, granules, or base makeup.

Polyphenols can be applied e.g., in varnishes, pesticides and in the production processes of drugs and synthetics. The use in different branches of industry cause high sale values (Obied et al., 2005) and make the recovery of these components from OMW attractive OMW has been proposed as a low-cost substrate for saccharides (or biopolymers) because of its special rheological properties, this biopolymer is widely used as thickener or viscosifier in food, cosmetics, pharmaceuticals, paper, paint, textiles, adhesives, biofilm, and tertiary oil recovery.

EXAMPLES

Experimental data disclosed herein demonstrate evidence of successful application of a novel and efficient method for isolating polyphenols from OMW to obtain biomolecules of interest for use in the food industry, cosmetic industry, or pharmaceutical industry.

The following experimental data provides those of ordinary skill in the art with a complete disclosure and description of how to make and use the methods of the invention, and are not intended to limit the scope of what the inventors regard as their invention. Standard techniques well known in the art or the techniques specifically described below were utilized.

Figure 1:
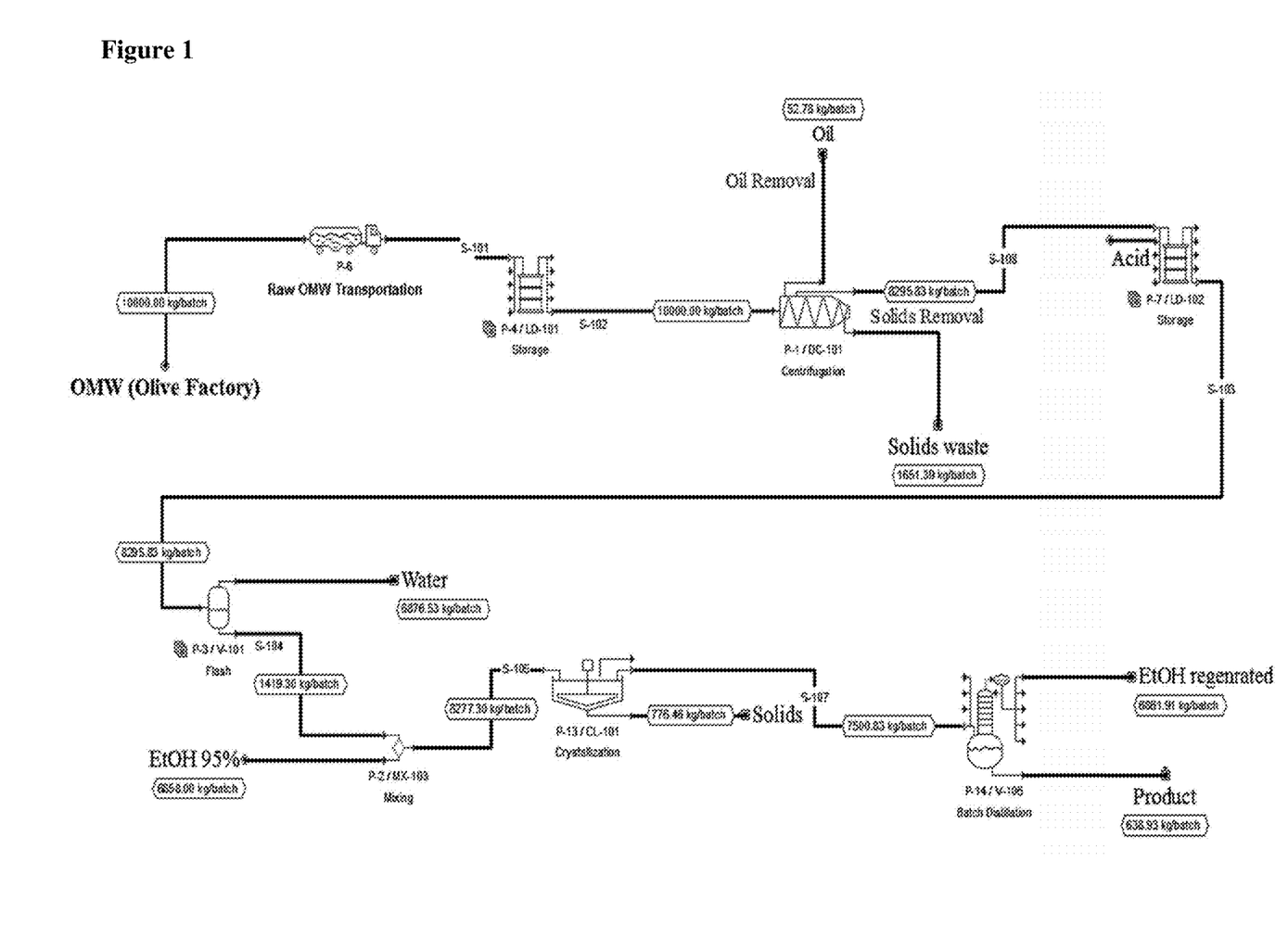
FIG. 1 shows the scheme of polyphenols production process flow pattern.

FIG. 1 shows a flow sheet scheme of the present invention for the production process of pure polyphenols from OMW. An OMW sample, produced according to a three-phase centrifugation process, was obtained from an olive oil continuous processing plant located in Sfax (southern Tunisia). The present invention contains different step of separation unit operation for the selection of polyphenols from the total dissolved solid contained in the initial feed solution. An initial centrifugation step allows removal of most suspended solids in the feed solution. Further, an evaporation step, before drowning-out process, provides a concentrated solution up to 60% (w/w) total dissolved solid. Mixing with EtOH (95% v/v) and drowning-out splitting a solid phase and liquid phase after solid/liquid equilibrium. Isolated polyphenols dissolved in an aqueous solution are produced after batch distillation, which regenerates EtOH solvent for later use.

As shown in FIG. 1, OMW obtained from an olive oil production facility is stored in a tank at 1000 kg/batch before processing. Further, a step of centrifugation with decanter centrifuge and rated throughput of 28.27 kg/h used for solid and oil/fat removal from a bulk solution. The resulting aqueous supernatant (8295.83 kg/batch) is isothermally concentrated using flash evaporation via flash drum with operating temperature of 42° C., using steam as heating agent, and an operating pressure of 0.15 bar. After two hours, a concentrated solution with mass flow rate of 1419.3 kg/batch is produced, and a condensed water phase of about 6877 kg/batch. This water phase can be used in food industry as ingredient. The concentrated phase is then mixed with 95% EtOH (v/v) with mass flow rate of 6858 kg/batch. The obtained mixed solution is subjected to an equilibrium step for crystallizing dissolved solids but not the polyphenols which remain dissolved in an EtOH phase. The equilibration step takes twelve hours for most solid/liquid equilibrium to take place. The obtained liquid phase undergoes batch distillation for regeneration of EtOH. The batch distillation occurs with a condenser and reboiler temperature of 10° C. and 45° C., respectively, and with an operating pressure of 0.15 bar, % molar distillated of volatile compound (comprising water and EtOH) at 85%, vapor rate at 1310 kmol/h, the reflux ratio fixed at 10 and the relative volatility of EtOH of 2.41 compared to water taken as reference compound.

The distillate and condensate stream flow rate is about 6862 kg/batch and 639 kg/batch, respectively. The condensate is the desired product which is enriched for the polyphenols compounds.

Figure 2:
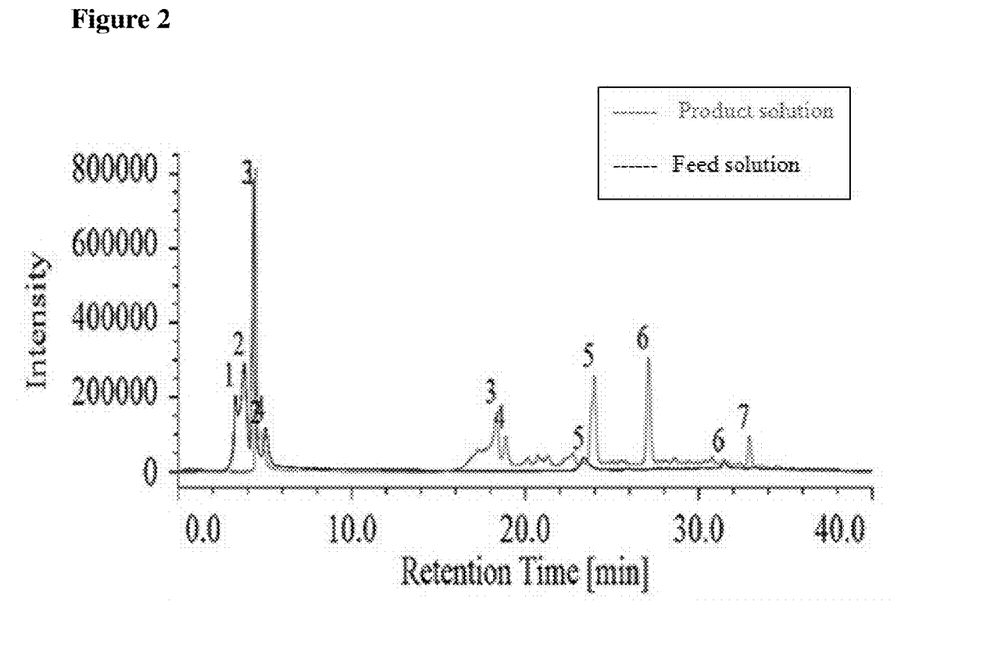
FIG. 2 shows the HPLC chromatogram for the feed and product solution.

FIG. 2 shows an HPLC chromatogram representing OMW feed of the present upstream process and the final product obtained after batch distillation step. The chromatogram shows the different peaks of hydroxytyrosol, oleuropein, and caffeic acid with a retention time 4 minutes, 21 minutes, and 33 minutes, respectively. High recovery of simple polyphenols from OMW feed in the final product was obtained after the integrated process of the present invention.

Figure 3:
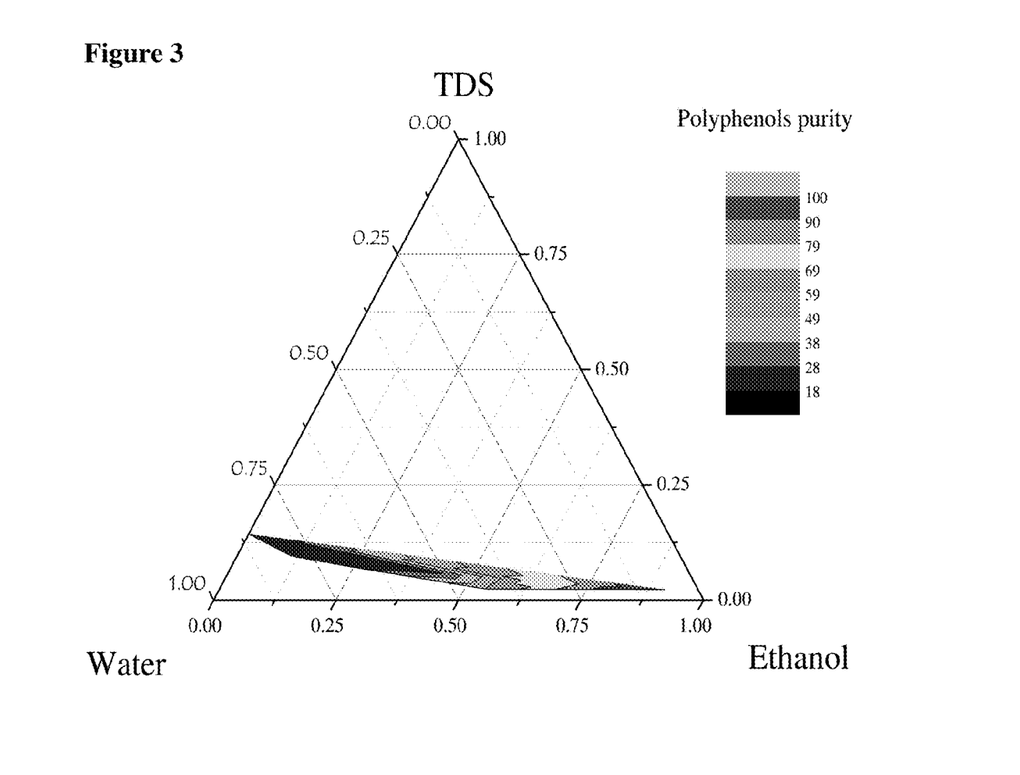
FIG. 3 shows the ternary phase diagram for experimental equilibrium value of total polyphenols purity after EtOH drowning-out process.

FIG. 3 shows a ternary phase diagram for the experimental value of total polyphenols purity after EtOH drowning-out process when the equilibrium step is twelve hours. Total purity of polyphenols is obtained for 90% (w/w) EtOH mass fraction in the system. Different polyphenols purity are obtained increasing gradually with increase of EtOH mass fraction in the system.

Figure 4:
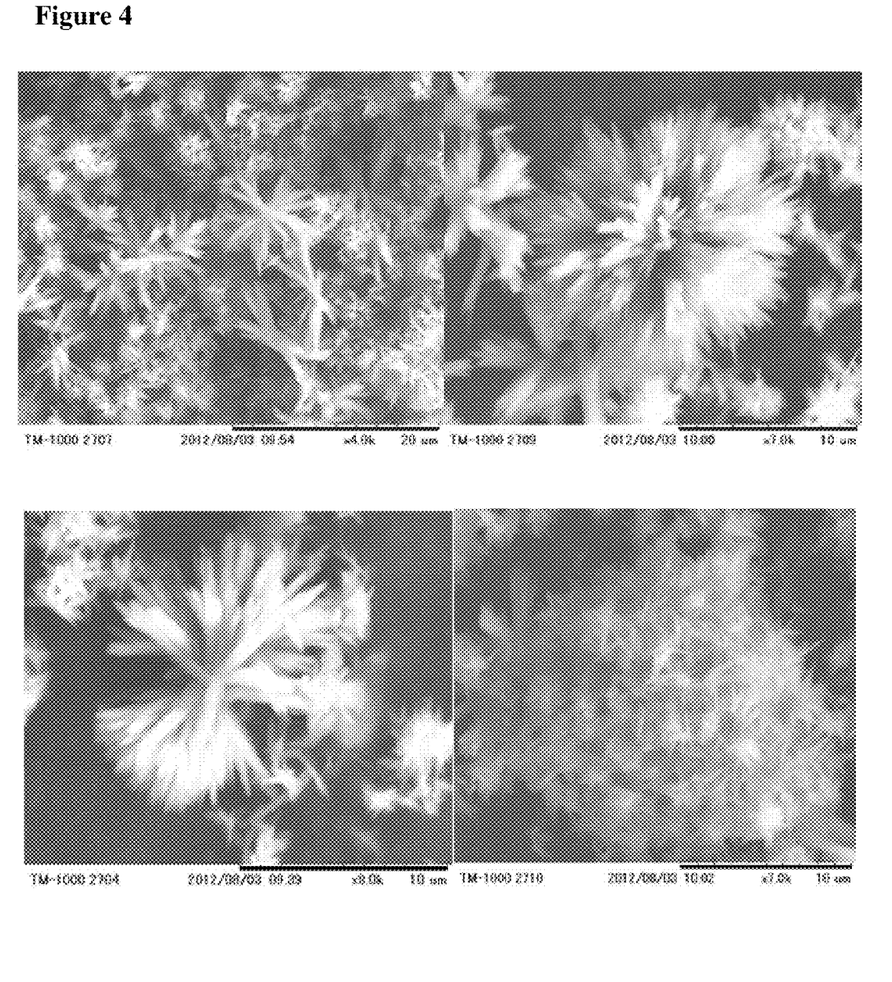
FIG. 4 shows the crystal morphology obtained after the drowning-out crystallization process in the obtained solid phase.

FIG. 4 shows the obtained solid phase in the drowning-out step. The crystals shown are obtained after two step of drowning-out crystallization-based process. The crystals have a lamellar shape and are of a small size. Very fine crystal slurries are obtained. Careful control of operating conditions give crystal products close in filterability to those produced by cooling crystallization.

FIGS. 5A to 5E show the stepwise operation and mass balance for each unit operation procedure of the overall invention.

Figure 5A:
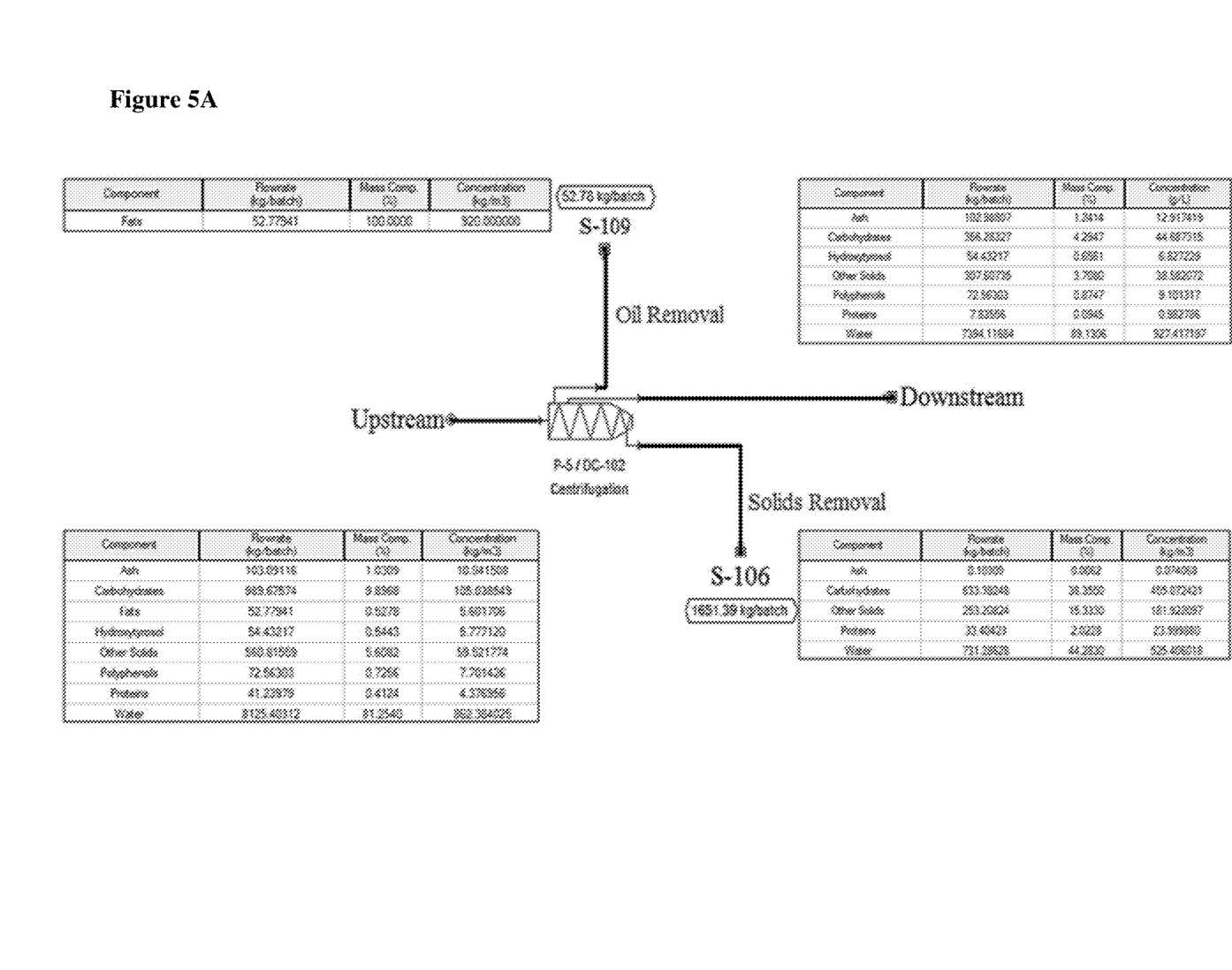
FIGS. 5A to 5E show the stepwise operation and mass balance of the process.

FIG. 5A shows the operating conditions and mass balance in the initial method steps. As shown, the chemical composition of OMW is mostly carbohydrate, which represents around 56% of total dry matter. Total polyphenols, which represents the target for recovery, represents only 2.35% of the total dry matter. The centrifugation step allows removal of particulate and oily components from the bulk solution. The operating condition was 5380×g within 30 minutes. The mass balance in the described process in described in Table 1 (below). The flow rate of the supernatant aqueous phase, oily phase and solid phase is 8296 kg/batch, 52.8 kg/batch, and 1651 kg/batch, respectively.

TABLE 1

Mass balance in centrifugation step
Removal of particulate and oily components

| Components | Oil components removal % | Solid components removal % |
|---|---|---|
| Ash | 0 | 0.1 |
| Carbohydrates | 0 | 64 |
| Fats | 100 | 0 |
| Others solid | 0 | 45.15 |
| Polyphenols | 0 | 0 |
| Proteins | 0 | 81 |
| TDS | 0 | 55 |
| Water | 0 | 9 |

Figure 5B:
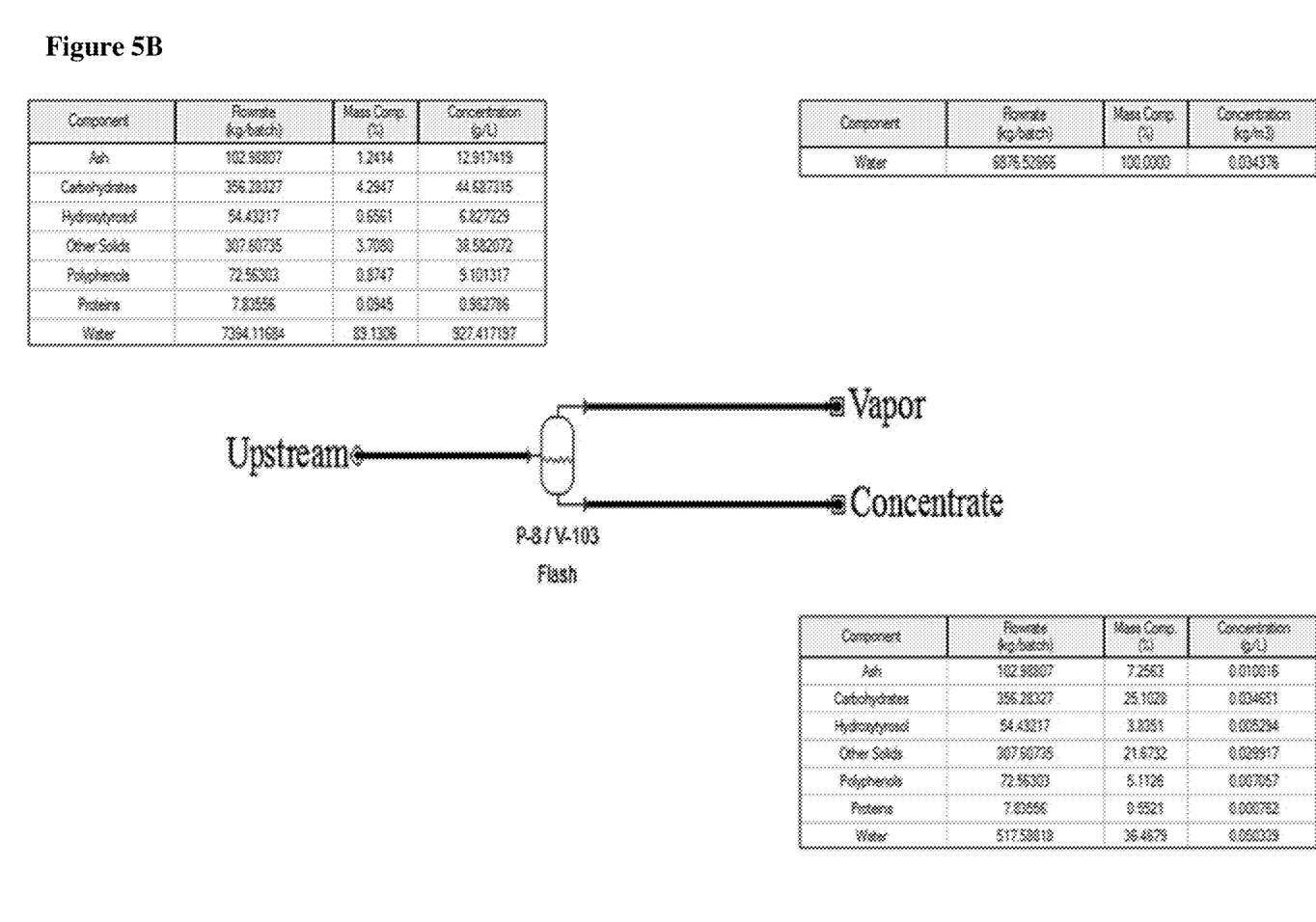

FIG. 5B shows the operating conditions and mass balance in the flash evaporation process. Here, "upstream" refers to the aqueous phase obtained after centrifugation. The "upstream" is concentrated by isothermal condition at 42° C., operating pressure 0.15 bar, water split to vapor of 93% (iv/iv), and process time 60 minutes. The flow rate of vapor outlet and liquid outlet was 6877 and 1419 kg/batch, respectively.

Figure 5C:
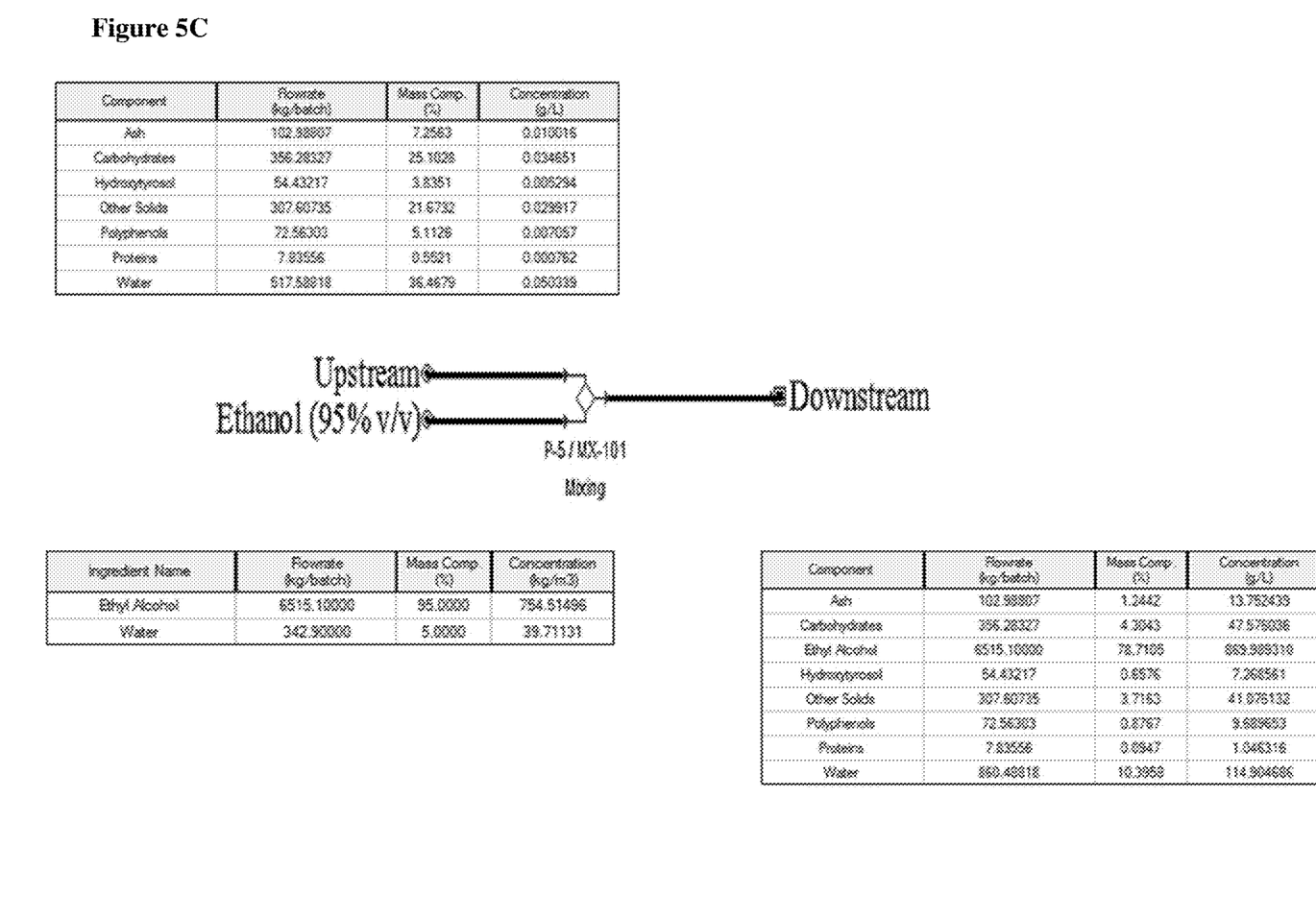

FIG. 5C shows the operating conditions and mass balance in the mixing step. After addition of EtOH to the stream (mass fraction percent 90%), polyphenols are isolated from others components. The operating condition has mass flow 99328 kg/h by unit operation within five minutes.

Figure 5D:
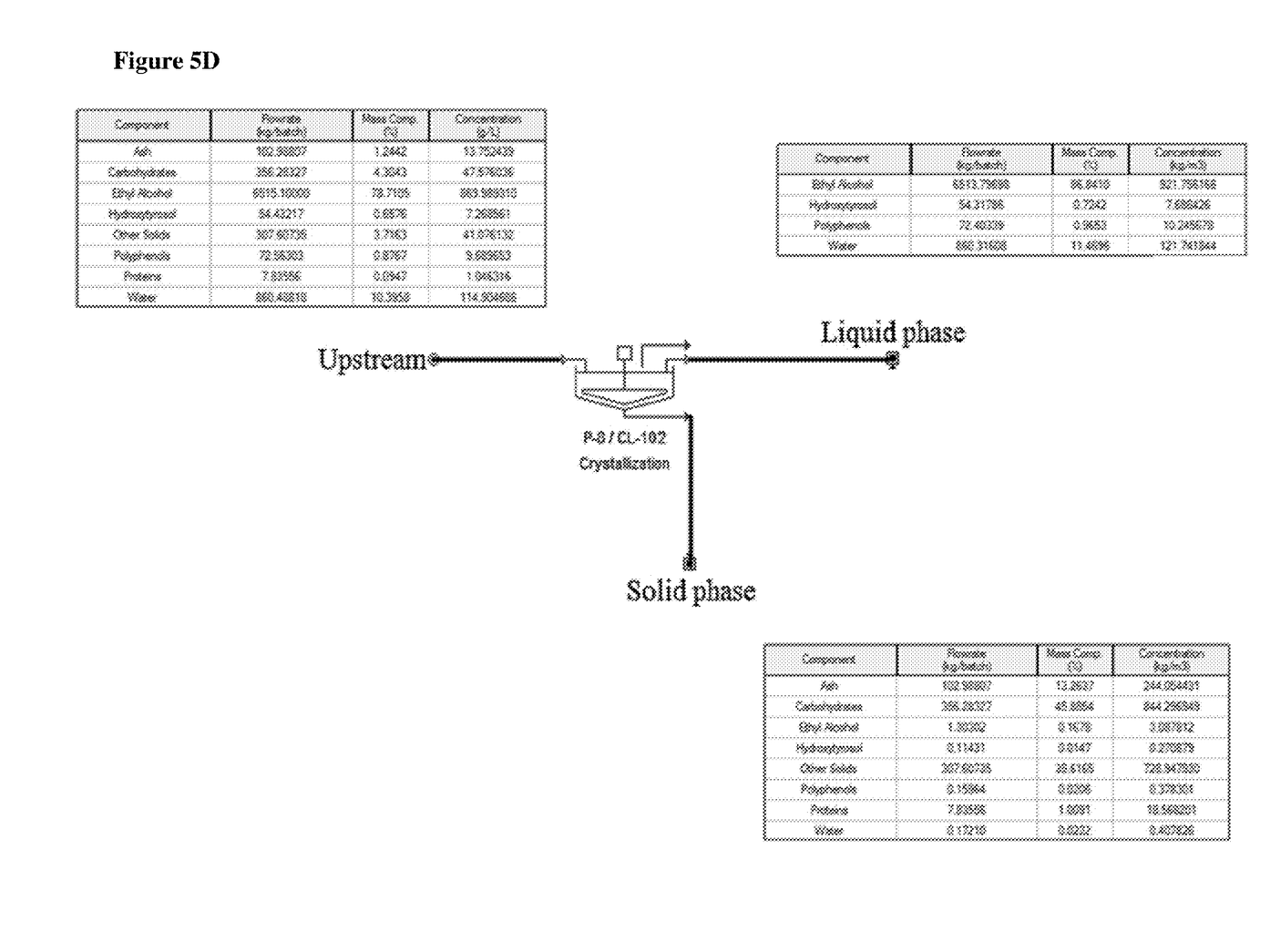

FIG. 5D shows the operating conditions and mass balance in the drowning-out/crystallization step. The equilibrium solid liquid splitting details are described in Table 2 (below).

TABLE 2

Mass balance in the drowning-out separation step
Solid/Liquid Splitting information

| Components | Crystallizable? | Removal % |
|---|---|---|
| Ash | Yes | 100 |
| Carbohydrates | Yes | 100 |
| Ethanol | No | 0.02 |
| Hydroxytyrosol | No | 0.21 |
| Others solid | Yes | 100 |
| Polyphenols | No | 0.22 |
| Proteins | Yes | 100 |
| Soluble solids | Yes | 88.97 |
| Water | No | 0.02 |

Further, the residence time of upstream solution in the operation was optimized within twelve hours for total isolation of polyphenols from the others soluble solids. The crystallization yield of crystallizable components at this range is nearly 100%. The crystallization temperature is room temperature, i.e., 25° C. The flow rate of feed, solid, and liquid phase is 8277 kg/batch, 776 kg/batch, and 7501 kg/batch, respectively.

Figure 5E:
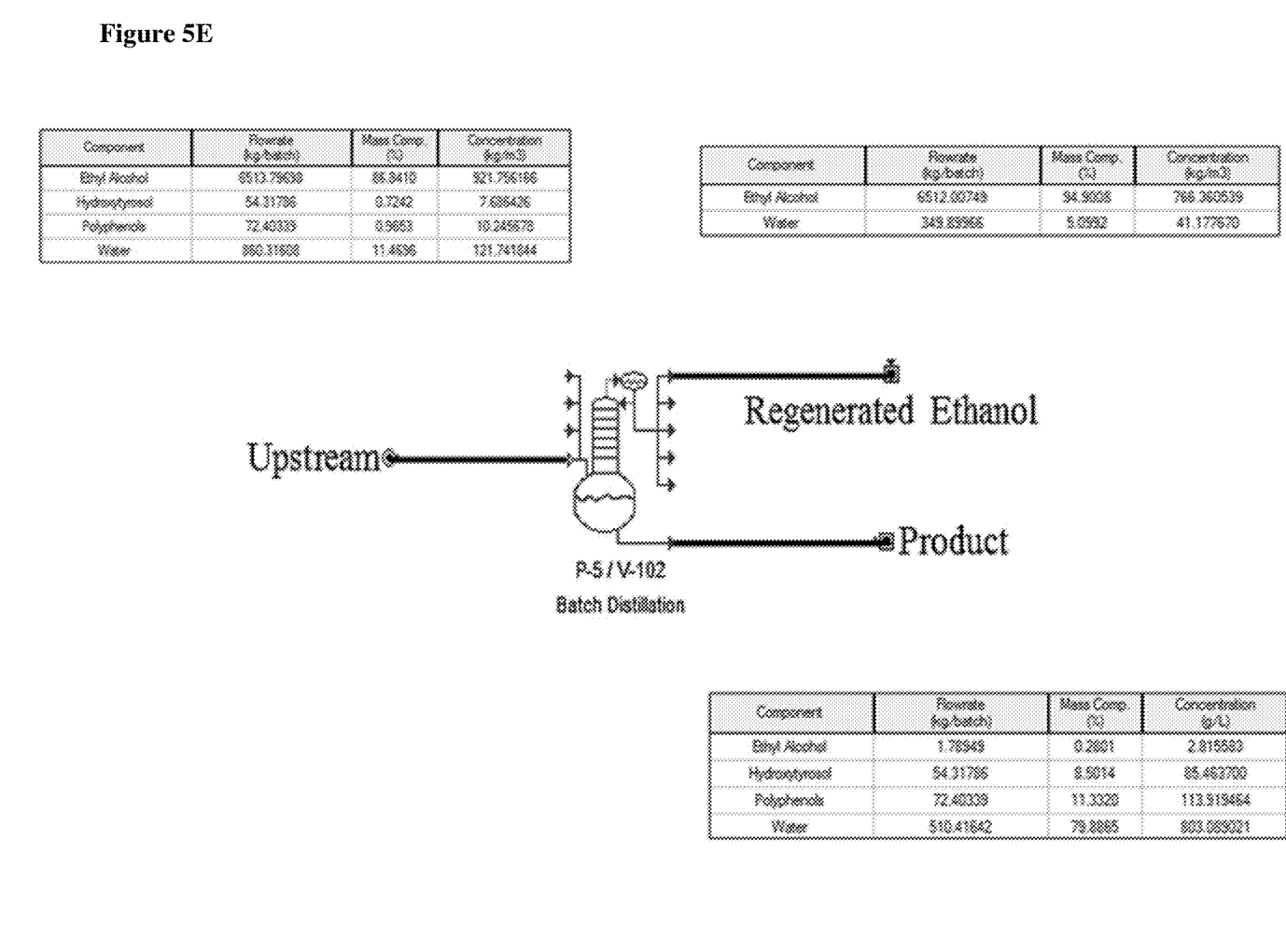

FIG. 5E shows the batch distillation process which allows regeneration of EtOH. This step improves the economic feasibility of the proposed invention since required EtOH is reused. This step operates at condenser temperature of 10° C., reboiler temperature of 45° C., operating pressure of 0.15 bar, reflux ratio fixed at 10, volume rate 1310 kmol/h, and the mol fraction of volatile components distilled at 85% with relative volatility of EtOH being 2.41 compared to water as reference component. The flow rate of the feed, distillate, and concentrate is 7501 kg/batch, 6862 kg/batch, and 639 kg/batch, respectively. 95% (v/v) EtOH is regenerated for use in the next batch of OMW processing.

Figure 6A:
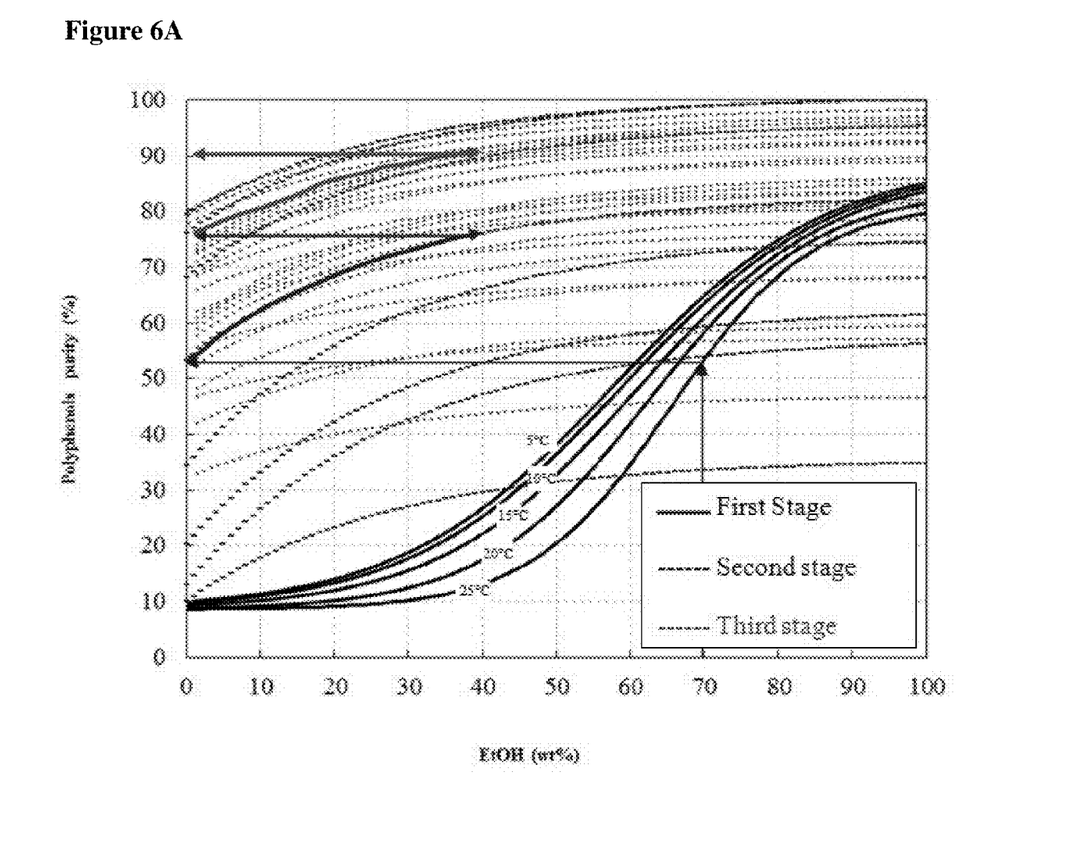
FIGS. 6A and 6B show the EtOH mass fraction-polyphenols purity diagram for the process.

FIG. 6A shows purity of the desired polyphenols correlated with the number of cycles and the EtOH mass fraction added during the drowning-out process. Up to three stages can be performed to reach high polyphenols purity using desired EtOH fraction in the process. The first stage is done at different temperature (5° C., 10° C., 15° C., 20° C., and 25° C., respectively), the purity of polyphenols is increased by decreasing the temperature with fixed EtOH mass fraction.

Figure 6B:
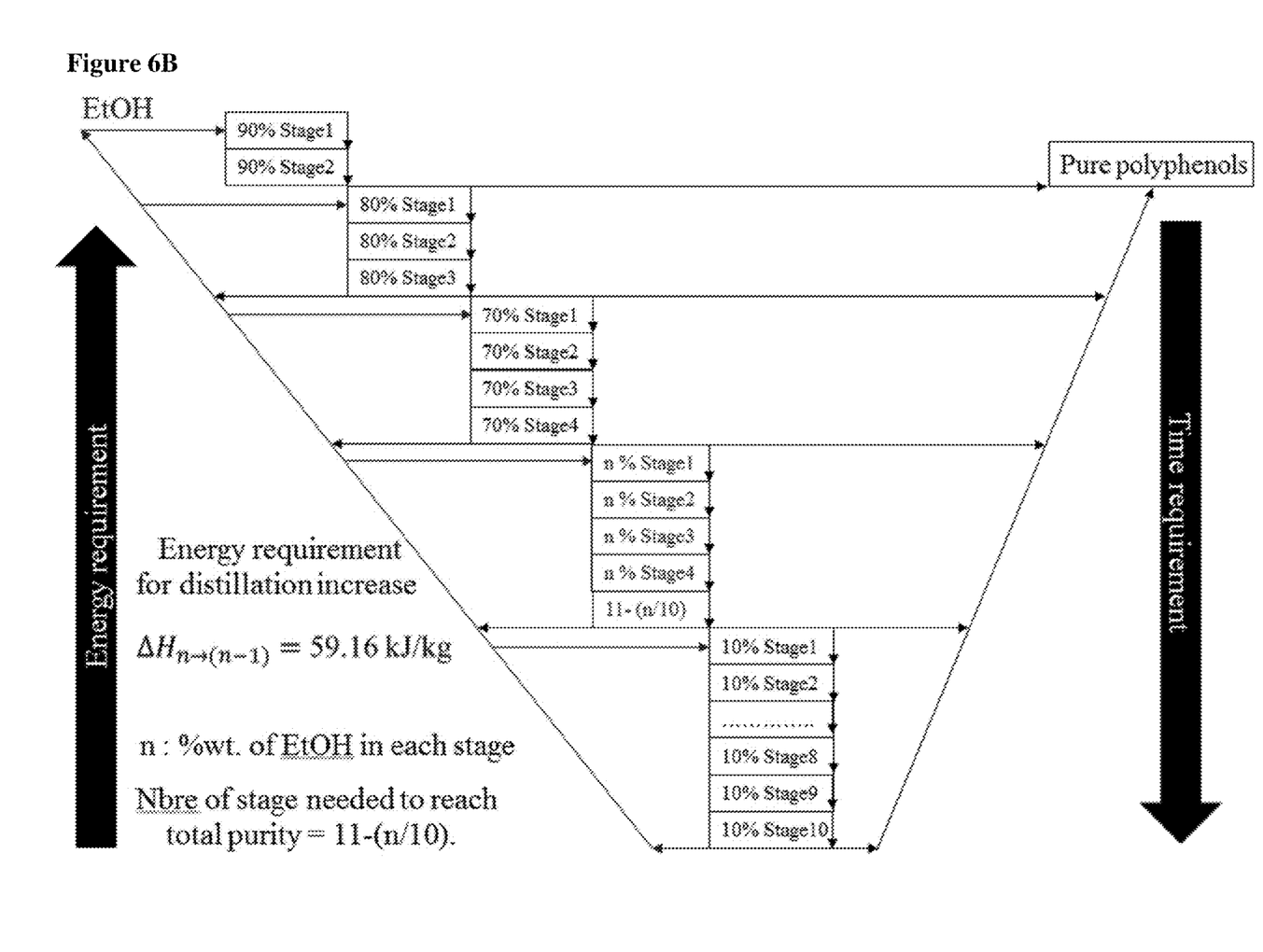

FIG. 6B shows that controlling the polyphenols purity in the process with mathematical model applied for controlling the process with crystallization temperature and EtOH mass fraction as design variables. The number of stages applied in the process represents a compromise between the energy requirement for distillation process, time requirement for production, and EtOH mass fraction applied to obtain high polyphenols purity.

Figure 7:
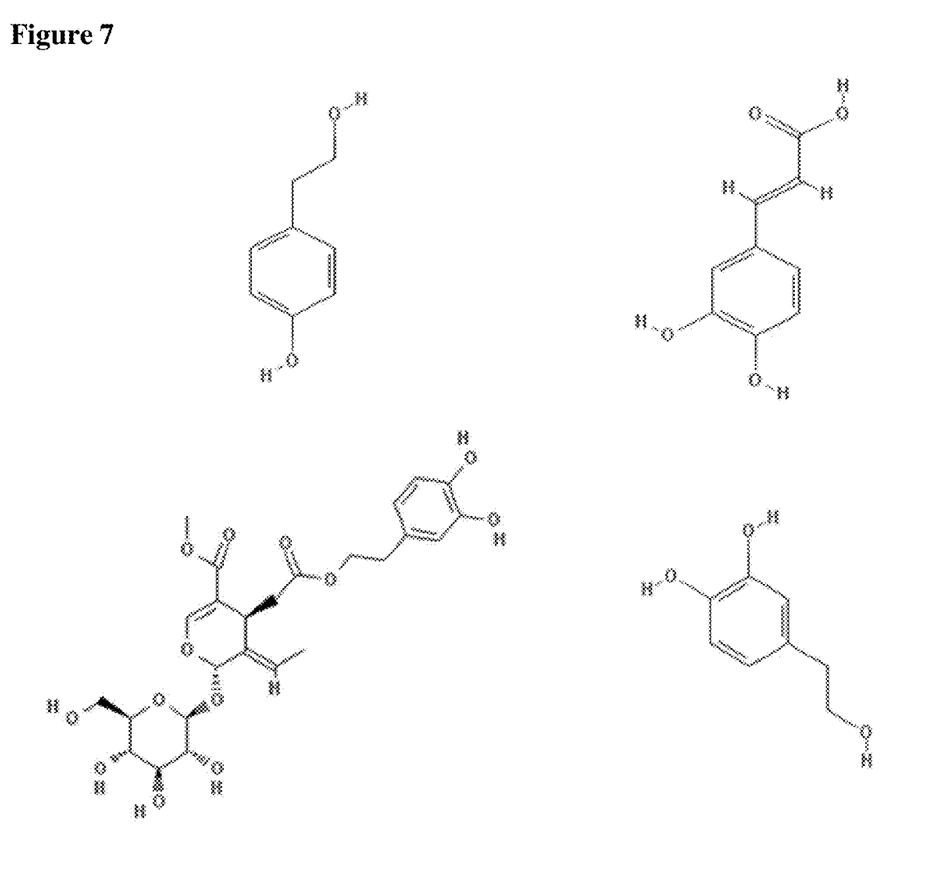
FIG. 7 shows the chemical structures of some polyphenols present in OMW.

FIG. 7 shows the chemical structures of some polyphenols present in OMW.

Using techniques well known in the art, water can be removed from the concentrated aqueous solution enriched of polyphenols obtained by the present invention, thereby providing a dried product.

The isolated polyphenols, and salts thereof, exhibit anti-oxidant, anti-microbial, anti-inflammatory, and anti-carcinogenic activities; they can be prepared as solid particles, as an aqueous solution, in an emulsion, or as lipidic-based nanoparticles. They can be used in the food industry, cosmetic industry, or pharmaceutical industry The Above Experimental Data were Obtained Using the Following Method and Materials:

Olive Mill Water Collection:

The OMW sample was delivered from an olive oil producing plant located in Sfax (southern Tunisia), during the harvest period. A three-phase continuous cycle modular machinery (Pieralisi system, Italy) was used for extracting olive oil.

pH Adjustment:

To avoid oxidation of the polyphenols contained in the OMW, its pH is lowered from the original value of 5.3 to 4.0 in order to deactivate the polyphenols oxidase present in OMW and to create optimum conditions for the stability of low molecular weight polyphenols. The pH is lowered by adding citric acid (10 g/L), which serves to protect polyphenol oxidation.

Centrifugation:

Centrifugation is carried out in batches, at a rotation speed of 5,380×g. After 15 minutes, three layers of material are separated: a supercritical film, made up of an oily emulsion, an intermediate rather opaque solution, and a dark deposit that stays at the bottom of the test tube.

The operation may be carried out by continuous centrifugation, preferably at 6,000×g, obtaining a partially clarified liquid that is then subjected to subsequent flash evaporation and a solid residue which may be used as fertilizer or compost along with other olive residues.

Drowning-Out Crystallization-Based Separation Process:

Drowning-out crystallization-based separation process relies on the addition of an extraneous component to effect a separation. This component may be a gas, a liquid, a supercritical fluid, or a solid. The component is often referred to as an anti-solvent, diluent, drowning-out agent, precipitant, salting-out, solventing-out, or watering-out agent. Like all crystallization processes, drowning-out can separate components that are difficult to distill. In addition, it offers two advantages over other crystallization techniques that rely on evaporation or temperature swings to obtain crystals. It is particularly suitable for the separation of heat sensitive materials because crystallization can often occur at or near ambient temperatures. The technique increases the yield of components whose solubility varies relatively little with temperature. U.S. Pat. No. 4,879,042 provides an example of a use for this method.

Flash Evaporation:

The solution is concentrated by a flash evaporator. Flash evaporation conditions are: Feed flow rate: 691 kg/h, Operating pressure: 0.15 bar, Operating temperature: 42° C., Process time: 60 min, Flow rate of concentrate: 118 kg/h, and Flow rate of water vapor: 573 kg/h.

High Performance Liquid Chromatography (HPLC) for Phenolic Monomer Quantifications:

Identification and quantification of phenolic monomers are carried out by HPLC. The assays described herein were performed on a JASCO apparatus composed of a PU-2089 plus pump and an UV-2075 plus UV/Visible detector. The column was a C-18 (4.6×150 mm; Shim-pack VP-ODS), and its temperature was maintained at 40° C. The flow rate was 0.5 mL/min. The mobile phase used was 0.1% phosphoric acid in water (A) versus 70% acetonitrile in water (B) for a total running time of 40 min, and the following proportions of solvent B were used for the elution: 5-25 min, 0-40%; 25-35 min, 25%; and 35-40 min, 40-50%. The flow rate was 0.5 mL/min, and the injection volume was 20 µL. Identification and quantification of oleuropein and hydroxytyrosol was based on its spectrum and on its retention time in comparison with standards analyzed under the same conditions.

Total Polyphenols Content Determination:

where $M_1$ the mass of the empty capsule, $M_2$ the mass of full capsule after drying at 105° C., V is the volume of sample in liters.

Olive oil production is generally connected to the generation of a number of adverse environmental problems including OMW. The annual production of OMW worldwide is estimated to be over 30 million m$^3$, 95% of which is produced in Mediterranean countries. Disposal of OMW represents a huge environmental problem, not only due to the large amounts of the produced residue, but also due to its specific chemical characteristics (Ntaikou et al. 2009). OWM's phytotoxicity and low biodegradability is mainly due to high COD and BOD contents, as well as to the presence of relevant amounts of polyphenols up to 10 g/L, (Mantzavinos and Kalogerakis 2005)), which are known to be toxic when at this concentration. The polyphenol fraction of olive oil comprises only 2% of the total polyphenols content of the olive fruits, with the remaining 98% being lost in OMW (Rodis et al. 2002). Thus, OMW can be a rich source of a diverse range of polyphenols with a wide array of biological activities for use in the food industry, cosmetic industry, or pharmaceutical industry (Moure et al. 2001; Schieber et al. 2001). Thus, the recovery of polyphenols from OMW represents an economically interesting strategy (Bertin et al. 2011; Ferri et al. 2011).

Several techniques are used individually or combined to recover polyphenols from OMW. These techniques largely comprise extraction, membrane separation, centrifugation, and chromatographic procedures. (See below)

| Comparison of Techniques Used for Recovery of Antioxidants from OMW | | | | | |
|---|---|---|---|---|---|
| Technique | Additional Chemicals | High Pressure | High Temperature | Phase Change | Application |
| Solvent extraction | Organic solvent | − | − | − | Individually or prior to membrane separation |
| SCF extraction | SCF preferably SC $CO_2$ | + | + | + | Individually or prior to membrane separation |
| Membrane separation | Membrane | + | − | − | After solvent extraction, usually in a sequential form |
| Column chromatography | Resin; regeneration solution; elution solvent | − | − | − | Individually or after solvent extraction or membrane separation, usually in a sequential form |

Concentration of total phenols was measured as gallic acid equivalents (Randhir and Shetty 2007). One milliliter of diluted sample was transferred to a test tube and 1 mL of 95% ethanol; 5 mL of distilled water, and 0.5 mL of Folin-Ciocalteu phenol reagent were added. After an incubation period of 5 min, 1 mL of 5% $Na_2CO_3$ was added, well mixed and kept in the dark for an hour. Then the samples were vortexed and the absorbance was measured at 725 nm using a UV spectrophotometer.

Dry Ashing:

Dry ashing is performed by placing the sample in an open inert vessel and destroying the combustible (organic) portion of the sample by thermal decomposition using a muffle furnace FO100 Yamato, Japan. Ashing temperature is 700° C.

The amount in grams of ash per liter is given by the expression:

$$(M_3-M_1)\times 100/V$$

where $M_1$ the mass of the empty capsule, $M_3$ mass of capsule after calcination at 600° C., and V is the volume of sample in liters.

Total Dissolved Solid (TDS):

TDS was determined by evaporating a sample in a porcelain dish at 105° C. for 24 hours, the amount in grams of total dissolved solids per liter is given by the expression:

$$(M_2-M_1)\times 100/V$$

Chromatography is presently the preferred procedure for isolating polyphenols from OMW, from the standpoint of ultimate product purity. However, the complexity, tediousness, and high cost of chromatography are powerful deterrents to its use on an industrial scale. Specific affinity sorbents are surely the most selective candidates for this technique, although they are usually costly, and frequently have short service-lifetime. Moreover, where bioactive substances are employed as affinity ligands, there are serious regulatory concerns about the possibility of detachment of such ligands (or their fragments) from the solid phase, and their contamination of the product. The possibility that these contaminants might be immunogenic or carcinogenic or otherwise toxic must be considered and properly addressed.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or sub combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

NON-PATENT PUBLICATIONS

Beckmann, W. (1999) Nucleation phenomena during the crystallisation and precipitation of Abecarnil. Journal of crystal growth 198, 1307-1314.

Berry, D. A., Dye, S. R. and Ng, K. M. (1997) Synthesis of drowning—out crystallization—based separations. AIChE Journal 43(1), 91-103.

Bertin, L., Ferri, F., Scoma, A., Marchetti, L. and Fava, F. (2011) Recovery of high added value natural polyphenols from actual olive mill wastewater through solid phase extraction. Chemical Engineering Journal.

Brittain, H. G. (1999) Polymorphism in pharmaceutical solids, M. Dekker New York.

Charmolue, H. and Rousseau, R. W. (1991) L-serine obtained by methanol addition in batch crystallization. AIChE Journal 37(8), 1121-1128.

Ferri, F., Bertin, L., Scoma, A., Marchetti, L. and Fava, F. (2011) Recovery of low molecular weight phenols through solid-phase extraction. Chemical Engineering Journal 166 (3), 994-1001.

Henley, E. J. and Seader, J. (1981) Equilibrium-stage separation operations in chemical engineering, Wiley New York.

Hyung, W., Kim, Y., Chung, C.-H. and Haam, S. (2008) Drowning-out crystallization of 1-proline: Effect of antisolvent composition and processing parameters on crystal size and shape. Powder technology 186(2), 137-144.

Mantzavinos, D. and Kalogerakis, N. (2005) Treatment of olive mill effluents: Part I. Organic matter degradation by chemical and biological processes—an overview. Environment international 31(2), 289-295.

Moure, A., Cruz, J. M., Franco, D., Domínguez, J. M., Sineiro, J., Domínguez, H., Jose Ntifiez, M. and Parajó, J. C. (2001) Natural antioxidants from residual sources. Food Chemistry 72(2), 145-171.

Myerson, A. (2002) Handbook of industrial crystallization, Butterworth-Heinemann.

Ntaikou, I., Kourmentza, C., Koutrouli, E., Stamatelatou, K., Zampraka, A., Kornaros, M. and Lyberatos, G. (2009) Exploitation of olive oil mill wastewater for combined biohydrogen and biopolymers production. Bioresource Technology 100(15), 3724-3730.

Obied, H. K., M. S. Allen, D. R. Bedgood, P. D. Prenzler and K. Robards et al. (2005) Bioactivity and analysis of biophenols recovered from olive mill waste. J. Agric. Food Chem., 53: 823-837.

Pennington, J. A. T. (2002) Food composition databases for bioactive food components. Journal of food composition and analysis 15(4), 419-434.

Randhir, R. and Shetty, K. (2007) Mung beans processed by solid-state bioconversion improves phenolic content and functionality relevant for diabetes and ulcer management. Innovative Food Science & Emerging Technologies 8(2), 197-204.

Rodis, P. S., Karathanos, V. T. and Mantzavinou, A. (2002) Partitioning of olive oil antioxidants between oil and water phases. Journal of Agricultural and Food Chemistry 50(3), 596-601.

Schieber, A., Stintzing, F. and Carle, R. (2001) By-products of plant food processing as a source of functional compounds—recent developments. Trends in Food Science & Technology 12(11), 401-413.

Schmitt, E. A., Law, D. and Zhang, G. G. (1999) Nucleation and crystallization kinetics of hydrated amorphous lactose above the glass transition temperature. Journal of pharmaceutical sciences 88(3), 291-296.

Szabó-Révész, P., Göczö, H., Pintye-Hódi, K., Eroš, I., Hasznos-Nezdei, M. and Farkas, B. (2001) Development of spherical crystal agglomerates of an aspartic acid salt for direct tablet making. Powder technology 114(1), 118-124.

Takaç, S. and Karakaya, A. (2009) Recovery of phenolic antioxidants from olive mill wastewater. Recent Pat. Chem. Eng. 2, 230-237.

Visioli, F. and Galli, C. (2002) Biological properties of olive oil phytochemicals. Critical reviews in food science and nutrition 42(3), 209-221.

Visioli, F., Poli, A. and Galli, C. (2002) Antioxidant and other biological activities of phenols from olives and olive oil. Medicinal Research Reviews 22, 65-75.

PATENT DOCUMENTS

CA2420893, EP1310175, EP1369407, EP1773721, EP811678, ES2051238, FR2825022, JP2000319161, US2002004077, US2002058078, US2002198415, U.S. Pat. No. 4,879,042, U.S. Pat. No. 6,358,542, U.S. Pat. No. 637, 969, U.S. Pat. No. 7,261,909, WO0145514, WO02064537, WO0212159, WO0218310, WO2005003037, and WO9747711.

What is claimed is:

1. A method for producing a polyphenol-enriched aqueous solution from olive mill water (OMW) comprising the following sequential steps:
   (a) obtaining an OMW after olive oil extraction from olive fruits;
   (b) pretreating the OMW by removing residual oil, large-sized organic compounds, particles, or soluble molecules from OMW thereby forming a more clear aqueous phase;
   (c) concentrating the aqueous phase thereby producing a concentrate;
   (d) mixing the concentrate with at least one solvent thereby producing a mixture;
   (e) transferring the mixture to a crystallization unit thereby producing a liquid phase and crystals in a solid phase; and
   (f) distilling the liquid phase in a distillation unit thereby evaporating the solvent and retaining the polyphenol-enriched aqueous solution.

2. The method of claim 1, wherein the concentrate of step (c) comprises hydroxytyrosol, oleuropein, caffeic acid, and other minor polyphenols.

3. The method of claim 2, wherein the final concentration of dissolved solids in the concentrate of step (c) is 40-70% (w/w) containing 60-90% organic matter fraction.

4. The method of claim 1, wherein the mixing step (d) occurs in one or more mixing modules.

5. The method of claim 1, wherein solid carbohydrates and solid salts are precipitated out in the crystallization unit of step (e).

6. The method of claim 4, wherein the one or more mixing modules and the crystallization unit have independently controllable environments including temperature, solvent mass fraction, and numbers of stages.

7. The method of claim 1, wherein a solid phase comprising a high content of salts and saccharides is crystallized in the crystallization unit.

* * * * *